(12) United States Patent
Chung et al.

(10) Patent No.: US 11,699,528 B2
(45) Date of Patent: Jul. 11, 2023

(54) FALLS RISK MANAGEMENT

(71) Applicant: Hill-Rom Services, Inc., Batesville, IN (US)

(72) Inventors: Chiew Yuan Chung, Singapore (SG); Kirsten Emmons, Batesville, IN (US); Matthew McCormick Riordan, Apex, NC (US); Karrie Browne, Batesville, IN (US); Yuan Shi, Singapore (SG); Eugene Urrutia, Durham, NC (US); Lori Ann Zapfe, Milroy, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 246 days.

(21) Appl. No.: 16/911,498

(22) Filed: Jun. 25, 2020

(65) Prior Publication Data
US 2020/0411198 A1    Dec. 31, 2020

Related U.S. Application Data

(60) Provisional application No. 62/868,394, filed on Jun. 28, 2019.

(51) Int. Cl.
*G16H 50/30* (2018.01)
*G16H 40/20* (2018.01)
(Continued)

(52) U.S. Cl.
CPC ............ *G16H 50/30* (2018.01); *A61B 5/1117* (2013.01); *A61B 5/7275* (2013.01); *G08B 21/043* (2013.01); *G08B 21/0461* (2013.01); *G08B 25/008* (2013.01); *G16H 10/60* (2018.01); *G16H 40/20* (2018.01)

(58) Field of Classification Search
CPC ........ G16H 50/30; G16H 40/20; G16H 10/60; A61B 5/1117; A61B 5/7275; G08B 21/043; G08B 21/0461; G08B 25/0008
(Continued)

(56) References Cited

U.S. PATENT DOCUMENTS

| | | | |
|---|---|---|---|
| 10,600,204 B1 * | 3/2020 | Rush | A61B 5/746 |
| 2011/0046498 A1 * | 2/2011 | Klap | A61B 5/6887 |
| | | | 600/534 |

(Continued)

FOREIGN PATENT DOCUMENTS

| | | |
|---|---|---|
| CA | 3039828 A1 | 4/2018 |
| CN | 106203512 A | 12/2016 |

(Continued)

OTHER PUBLICATIONS

Extended European Search Report dated Oct. 27, 2020, pp. 9.

*Primary Examiner* — Michael Tomaszewski
*Assistant Examiner* — Rachael Sojin Stone
(74) *Attorney, Agent, or Firm* — Merchant & Gould P.C.

(57) ABSTRACT

Automatically gathering and processing data relating to risk of patient falls. The data is analyzed to determine a level of risk each patient has for falling. Patient risk for falls is stratified and protocols are implemented to mitigate that risk. The system communicates instructions and alerts to caregivers to complete tasks or provide aid to patients. Updates to patient medical information and updates to best practices in fall risk management result in updates to patient risk stratifications. In turn, tasks and alerts are updated to reflect updates to patient risk stratifications.

17 Claims, 14 Drawing Sheets

(51) Int. Cl.
 *G16H 10/60* (2018.01)
 *A61B 5/11* (2006.01)
 *A61B 5/00* (2006.01)
 *G08B 21/04* (2006.01)
 *G08B 25/00* (2006.01)

(58) Field of Classification Search
 USPC .............................................................. 705/3
 See application file for complete search history.

(56) References Cited

U.S. PATENT DOCUMENTS

| | | | | |
|---|---|---|---|---|
| 2012/0314901 | A1* | 12/2012 | Hanson | G16H 40/67 |
| | | | | 600/595 |
| 2013/0127620 | A1* | 5/2013 | Siebers | A61B 5/1113 |
| | | | | 340/573.1 |
| 2014/0022079 | A1 | 1/2014 | Wilson et al. | |
| 2015/0109442 | A1 | 4/2015 | Derenne et al. | |
| 2016/0058330 | A1 | 3/2016 | Menzel | |
| 2016/0220153 | A1 | 8/2016 | Annegarn et al. | |
| 2016/0350489 | A1* | 12/2016 | Ribble | G16H 40/20 |
| 2020/0066415 | A1* | 2/2020 | Hettig | G16H 40/63 |
| 2022/0202314 | A1* | 6/2022 | Larson | A61B 5/7282 |

FOREIGN PATENT DOCUMENTS

| | | |
|---|---|---|
| CN | 109643585 A | 4/2019 |
| EP | 3346402 A1 | 7/2018 |
| EP | 3398513 A1 | 11/2018 |
| WO | 2018037026 A1 | 3/2018 |
| WO | 2018/069262 A1 | 4/2018 |

\* cited by examiner

FALLS RISK MANAGEMENT

RELATED APPLICATION(S)

This patent application claims the benefit of U.S. Patent Application Ser. No. 62/868,394 filed on Jun. 28, 2019, the entirety of which is hereby incorporated by reference.

BACKGROUND

Patients in care facilities, such as hospitals, clinics, nursing homes or the like, are often in compromised medical conditions. Injuries sustained by patients due to falls in care facilities result in significant healthcare costs. In an effort to prevent such injuries, various protocols are implemented to mitigate the risks. For example, patients who are at risk of falling when moving unassisted may be identified as fall risks, and certain protocols may be implemented to reduce the opportunity for the patients to move about the room unassisted.

It is difficult to accurately assess the likelihood that a patient will fall. Accurate prediction of fall risk is important for efficient allocation of hospital resources to prevent falls. Accurate assessment of fall risk requires consideration of a large number of contributing factors. New research is continually updating the body of knowledge regarding risk factors and how to weigh each one. In order to provide the best fall risk assessment, the method used must reflect the latest research.

SUMMARY

Embodiments of the disclosure are directed to a system for automatically assessing patient fall risk. The system includes at least one processor and memory encoding instructions which, when executed by the at least one processor, cause the at least one processor to: a) automatically aggregate falls-related data for a patient from one or more healthcare information systems; b) access falls-related rules for a healthcare facility administering care to the patient, the falls-related rules defining criteria for fall risk stratifications and protocols for each fall risk stratification; c) stratify fall risk of the patient based on healthcare facility falls-related rules and falls-related data associated with the patient; d) automatically generate tasks and alerts based on the fall risk stratification of the patient and the healthcare facility falls-related rules; and e) repeat steps a-d until the healthcare facility is no longer administering care to the patient.

In another aspect, one or more computer-readable media having computer-executable instructions embodied thereon that, when executed by one or more computing devices, cause the computing devices to: receive intake information for a patient at a healthcare facility; access any available medical information for the patient; access falls-related rules for the healthcare facility, the falls-related rules defining fall risk stratifications and protocols for preventing falls; before receiving a fall risk score input from a caregiver analysis, determine a fall risk stratification for the patient based on the intake information, available medical information for the patient, and falls-related rules for the healthcare facility; communicate patient fall risk stratification to one or more caregiver communication systems; and generate and communicate one or more tasks to one or more caregivers assigned to the patient through the one or more caregiver communication systems, the tasks being generated based on the falls-related rules.

In yet another aspect, a computer-implemented method of managing patient fall risk in a healthcare facility comprises: a) automatically aggregating, at a fall risk management system, falls-related data for a patient from one or more healthcare information systems; b) accessing, from a rules data store, falls-related rules for a healthcare facility administering care to the patient, the falls-related rules defining criteria for fall risk stratifications and protocols for each fall risk stratification; c) stratifying fall risk of the patient based on healthcare facility falls-related rules and falls-related data associated with the patient; d) automatically generating and communicating tasks and alerts to one or more devices, the tasks and alerts being based on the fall risk stratification of the patient and the healthcare facility falls-related rules; and e) repeating steps a-d until the healthcare facility is no longer administering care to the patient.

The details of one or more techniques are set forth in the accompanying drawings and the description below. Other features, objects, and advantages of these techniques will be apparent from the description, drawings, and claims.

DETAILED DESCRIPTION

The present disclosure is directed to systems and methods for automatically gathering and processing data relating to risk of patient falls. The data is processed to determine a level of risk a patient has for falling and automatically implementing protocols to mitigate that risk. The system communicates instructions and alerts to caregivers to complete tasks or provide aid to patients.

Figure 1:
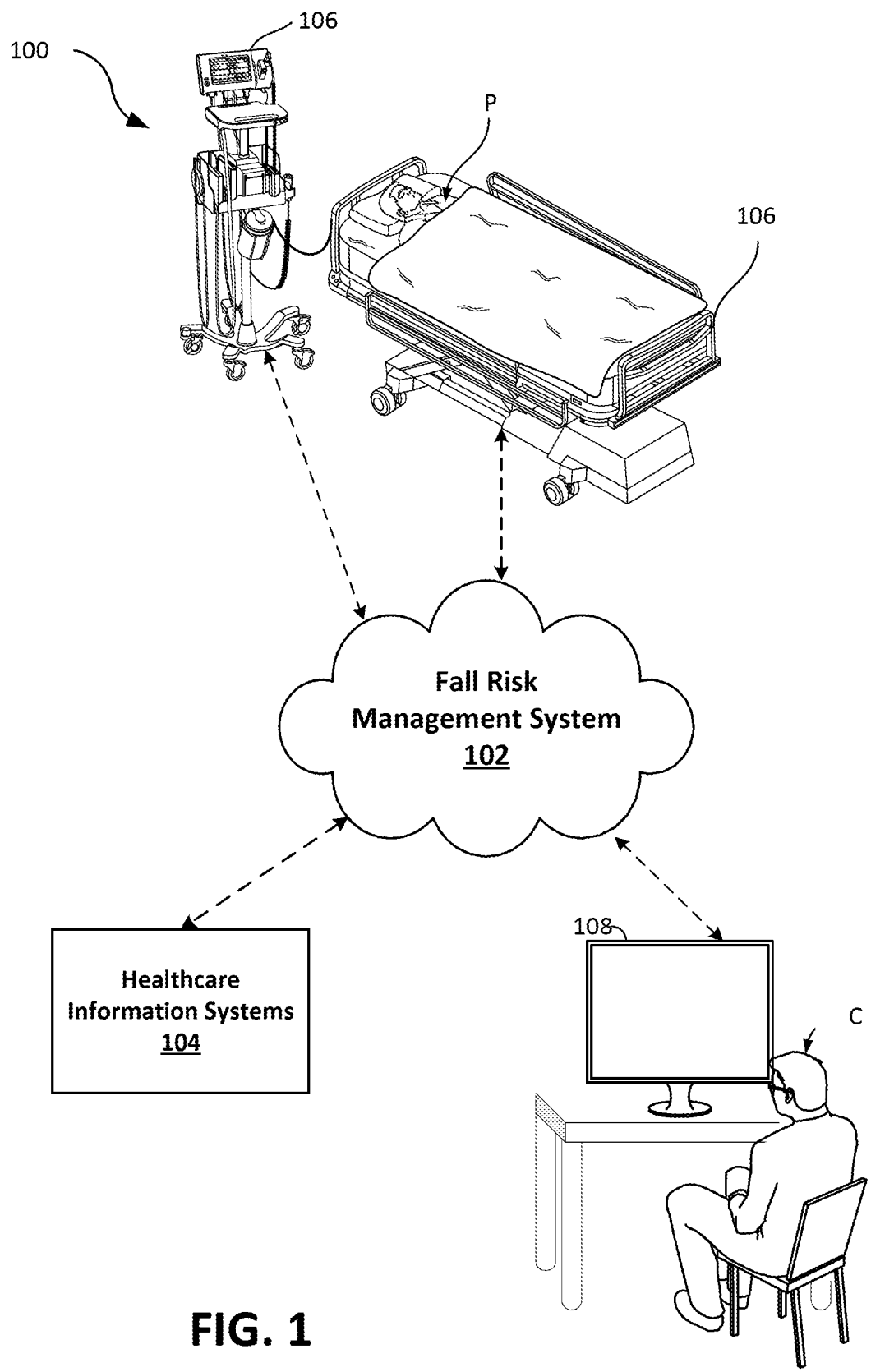
FIG. 1 is a block diagram schematically illustrating a healthcare facility that includes a fall risk management system.

FIG. 1 is a schematic diagram illustrating a healthcare facility 100 that includes a fall risk management system 102. The fall risk management system 102 operates to gather falls-related data from multiple information sources within the healthcare facility 100 to automatically update fall risk levels for patients P within the healthcare facility 100. In the example of FIG. 1, the fall risk management system 102 is in communication with healthcare information systems 104, patient monitoring devices 106, and caregiver communication systems 108.

One fall risk management system 102 can be communicating with multiple devices that are monitoring multiple patients P within the healthcare facility 100. In some embodiments, one fall risk management system 102 monitors information from devices for all patients within a healthcare facility 100. Healthcare information systems 104 can include electronic medical record (EMR) systems, ADT (admit, discharger, transfer) systems, and other hospital information systems. Examples of patient monitoring devices 106 include spot monitors, mattress pad devices, vitals sign monitoring devices, and smart beds. Caregiver communication systems 108 can include nurse call systems, caregiver mobile applications, and dashboards. Further details regarding the fall risk management system 102 are provided in the description of FIG. 2 below.

In one embodiment, the fall risk management system 102 is a cloud-based system that is hosted over the Internet. In this example embodiment, the fall risk management system 102 is accessible from a computer workstation via a web portal that provides a single sign-on configuration application.

In an alternative embodiment, the fall risk management system 102 is part of a local area network and is stored onsite in the healthcare facility 100. In this example embodiment, the fall risk management system 102 is accessible from a computer workstation via an intranet portal that provides a single sign-on configuration application.

Figure 2:
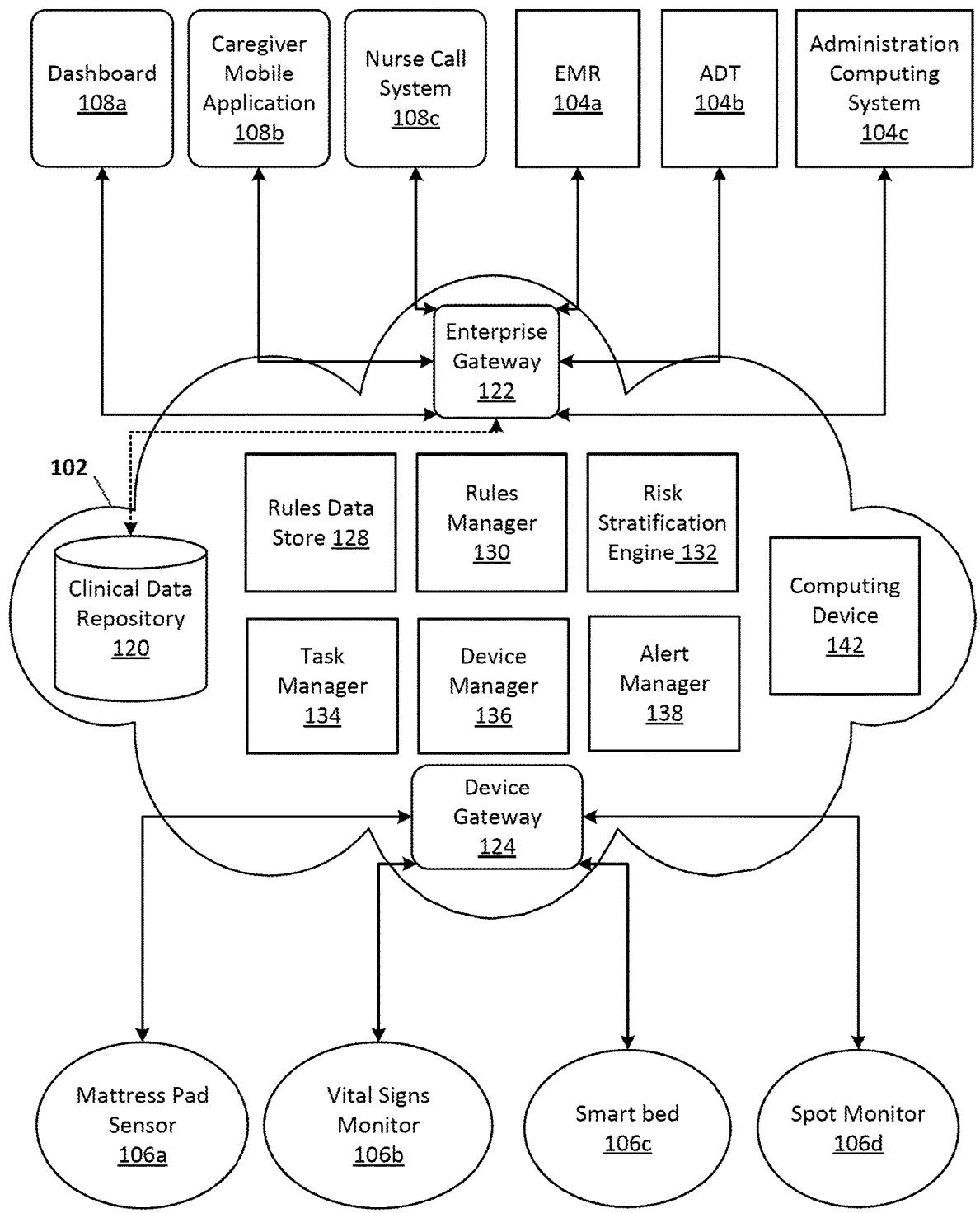
FIG. 2 is a block diagram providing a detailed schematic illustration of the fall risk management system of FIG. 1.

FIG. 2 is a more detailed schematic block diagram of an example fall risk management system 102 and the devices and information systems that the fall risk management system 102 communicates with to gather information about patient fall risk, stratify patients, and generate instructions to caregivers and devices to mitigate the risk of falls. The fall risk management system 102 can operate to serve a particular healthcare facility such as a hospital, nursing home, ambulatory surgical center, or rehabilitation center. The fall risk management system 102 could also operate to monitor patients outside of a healthcare center, such as patients recovering at home and using sensors to monitor their health.

In the example of FIG. 2, the fall risk management system 102 includes an enterprise gateway 122 and a device gateway 124. The enterprise gateway 122 enables transport and protocol conversion from one system to another. For example, the enterprise gateway 122 enables the fall risk management system 102 to receive information from an EMR system 104 and an ADT system 104b, process that information, and then communicate alert information to a caregiver mobile application 108b as well as nurse call systems 108c. The device gateway 124 allows the fall risk management system 102 to communicate with various devices such as a vital signs monitor 106c and a smart bed 106c. In some embodiments, the device gateway 124 also communicates through the enterprise gateway 122. In some embodiments, there are two device gateways 124: one for vital sign monitoring devices and one for bed devices.

Communications made through the enterprise gateway 122 and device gateway 124 can be performed using various languages and communication protocols. Generally, a TCP/IP protocol is utilized to communicate between the information sources, devices, and the fall risk management system 102. Some examples of communication protocols that work on top of the TCP/IP protocol include health level 7 (HL7) messaging standard, message queuing telemetry transport (MQTT) ISO standard, and fast healthcare interoperability resources (FHIR) standard.

The enterprise gateway 122 is in communication with one or more caregiver communication systems 108, data repositories 120, and healthcare information systems 104. In the example of FIG. 2, The enterprise gateway 122 is communicating with a dashboard 108a, a caregiver mobile application 108b, nurse call systems 108c, a clinical data repository 120, an electronic medical record (EMR) system 104a, an admit/discharge/transfer (ADT) system 104b, and an administration computing system 104c. Each healthcare facility might have different systems connecting to the fall risk management system 102 through the enterprise gateway 122. In some embodiments, the clinical data repository 120 does not need to communicate through the enterprise gateway 122 because it is hosted on the same cloud as the rest of the fall risk management system 102. In some embodiments, the clinical data repository 120 is hosted separately from the fall risk management system 102.

The dashboard 108a (or status board) provides an electronic display of information for one or more patients within a healthcare facility. Information that can be displayed includes patients' fall risk stratification, patients' fall risk scores, alerts, alarms, assigned caregivers, and changes in status.

The caregiver mobile application 108b is a computing application that operates on mobile devices assigned to caregivers. The caregivers can easily access information about patients and receive communications through the application. Caregivers can use the mobile application 108b to review patients' fall risk levels including details about why the patient is assigned to that level of risk. The caregiver mobile application 108b can also operate to communicate SBAR reports to other caregivers when shifts change.

The nurse call system 108 coperate to field calls from patients when they need assistance. In some embodiments, nurse call systems 108c receive calls from other systems within a healthcare environment based on various alerts triggered by connected devices such as a patient smartbed. One example of a call system is a CONNEX® Central Station from Welch Allyn, Inc., New York. Another example is NaviCare Nurse Call from Hillrom™.

The clinical data repository 120 operates to store clinical data for a healthcare facility. The clinical data includes patient information from laboratory analyses, allergy information, medication information, and other information relevant to the patient's health. The clinical data repository 120 can also store aggregated and anonymized patient data for identifying trends within the healthcare facility. These trends can inform the rules that are implemented to prevent patient falls. In some embodiments, the clinical data is not anonymized and is used for risk stratification and data display for particular patients.

The electronic medical record (EMR) system 104a operates to record information relevant to the medical history of each patient. Examples of information that might be stored in a patient's EMR includes lab results, surgical history, family medical history, current medications, and previous medical diagnoses. A patient's fall risk score (as determined by e.g. Morse Fall Scale, Johns Hopkins Fall Risk Assessment Tool) is another piece of information that could be added to an EMR. Examples of electronic medical records systems 110 include those developed and managed by Epic Systems Corporation, Cerner Corporation, Allscripts, and Medical Information Technology, Inc. (Meditech).

The admit/discharge/transfer (ADT) system 104b operates to record, store, and communicate information about patient demographics as well as admission/discharge status and location status for patients. The ADT system 104b provides real-time information on each patient admitted to the healthcare facility 100 including the patient's name, address, gender, room assignment within the healthcare facility 100, the date and time when admitted to and discharged from the healthcare facility 100, and whether the patient has been transferred to another room or department within the healthcare facility 100. In some cases, the level of urgency of the patient's visit can be indicated based on which department the patient is admitted to (e.g. emergency department).

The administration computing system 104c is a computing system utilized to oversee the operation of the healthcare facility. Healthcare administrators can view and modify information about healthcare facility policies including rules for mitigating fall risk and responding to fall incidents. The administration computing system 104c can also be used to access reports and information about patient falls and caregiver compliance with facility procedures for mitigating fall risk.

The device gateway 124 is in communication with one or more patient monitoring and support devices 106. In the example of FIG. 2, the device gateway 124 communicates with a mattress pad sensor 106a, a vital signs monitor 106b, a smart bed 106c, and a spot monitor 106d. One fall risk management system 102 might be in communication with a plurality of different monitors for each patient within a healthcare facility. Some facilities might have more or fewer devices available for monitoring and supporting patients.

The mattress pad sensor 106a operates to detect the weight distribution of a patient. It is placed on top of or under a mattress on a patient bed. In some instances, the sensor is built into the mattress. Shifts in the weight distribution detected by the mattress pad sensor 106a can indicate that a patient is getting out or falling out of bed. In some examples, the mattress pad device is an EarlySense® system.

The vital signs monitor 106b monitors various indicators of health for a patient such as heart rate, blood pressure, blood oxygen level, and respiration rate. One example of a patient monitoring device is the CONNEX® Vital Signs Monitor available from Welch Allyn, Inc., New York.

The smart bed 106c can include various functionalities to monitor patient behavior and health. For example, a smart bed 106c could monitor heart rate and respiratory rate when the patient is in the bed. Examples of smart beds 104 include Centrella® Smart+ bed, Progressa® bed system, or VersaCare® Med Surg Bed, each available from Hill-Rom Services, Inc., Batesville, Ind.

The spot monitor 106d operates to display vital signs from attached sensors such as blood pressure and body temperature. One example of a spot monitor 106d is the CONNEX® Spot Monitor available from Welch Allyn, Inc., New York.

The fall risk management system 102 further includes a rules data store 128, a rules manager 130, a risk stratification engine 132, a task manager 134, a device manager 136, an alert manager 138, and a computing device 142. Each of these components of the fall risk management system 102 performs operations that rely on information received through the enterprise gateway 122 or device gateway 124 and/or provides information to systems or devices through the enterprise gateway 122 or device gateway 124. In some embodiments, the rules manager 130, risk stratification engine 132, task manager 134, and alert manager 138 are all part of one module or engine that manages the collective functions.

The rules data store 128 operates to store rules and protocols defined by the healthcare facility for assessing falls risk, preventing falls, responding to falls, and reporting fall incidents. In some embodiments, rules within the rules data store 128 are updated as new data and research are received regarding falls-related risk factors and efficacy of prevention measures. Updates to rules can be received from the administration computing system 104c in some embodiments.

The rules manager 130 operates to access protocols for fall prevention and determine which rules apply to each patient. The rules manager 130 provides instructions to the risk stratification engine 132, task manager 134, device manager 136, and alert manager 138 to implement the rules and procedures for managing fall risk in a healthcare facility.

The risk stratification engine 132 operates to calculate a fall risk score for each patient. The fall risk score can be based upon a nurse assessment such as the Morse Fall Scale. In the event that a patient has not yet had a nurse assessment (due to just being admitted, etc.), a fall risk score can be generated based upon patient demographic information and other medical information available for the patient. The risk stratification engine 132 uses these fall risk scores along with the rules defined by the rules manager 130 to stratify each patient into a different risk category for falls. In some embodiments, a fall risk score is calculated by a clinical decision support (CDS) system and the risk stratification engine 132 utilizes the score to determine a risk category for a patient.

The task manager 134 operates to generate tasks that need to be completed to address patients that have changed risk stratification or to comply with fall prevention protocols. The task manager 134 notifies caregivers of tasks that need to be completed. In some instances, the tasks will be automatically assigned to caregivers through these communication channels based on caregiver roles and assignments. In some embodiments, the task manager 134 communicates through one or more of the dashboard 108a, caregiver mobile application 108b, and nurse call systems 108c.

The device manager 136 operates to generate commands to particular devices 106 through the device gateway 124. Some patient support devices 106 can be programmed to automatically perform tasks or adjustments to reduce a patient's risk of fall. For instance, if a patient's risk stratification becomes higher, the device manager 136 can communicate a command to a smart bed 106c to enable bed rails and a bed exit alarm.

The alert manager 138 operates to detect events from patient support devices 106 indicating that a patient needs immediate attention and communicates alarms or alerts to caregivers. The alert manager 138 operates based on rules generated by the rules manager 130 and patient fall risk stratifications generated by the risk stratification engine 132. Examples of alerts include alerting a caregiver when a bed sensor indicates that a patient with a high fall risk is likely to be getting out of bed.

The computing device 142 operates to execute software programs and access data. The computing device 142 includes at least a processor and memory. A more detailed view of an example computing device 142 is provided in FIG. 14.

Figure 3:
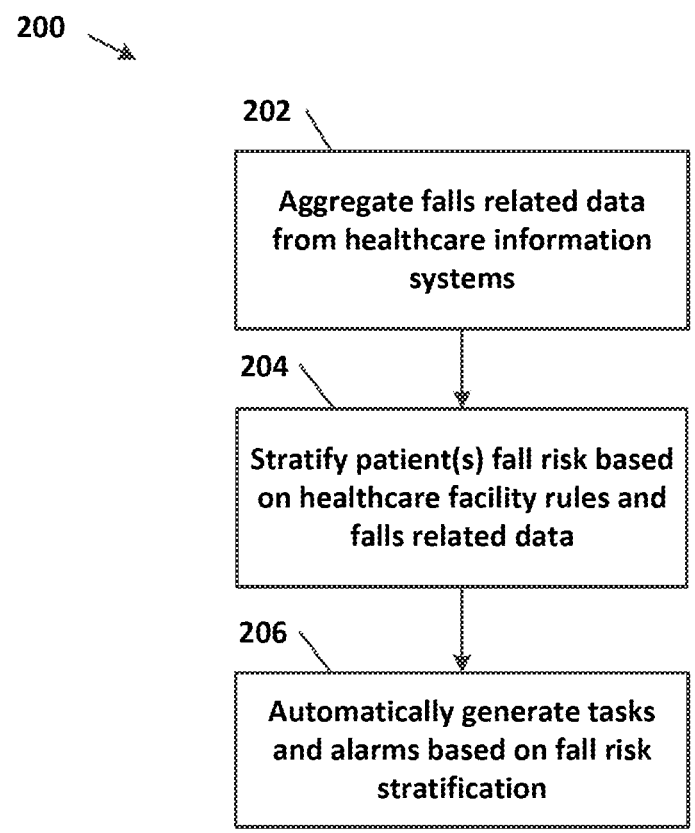
FIG. 3 is a flow chart illustrating a general example method of automatically assessing patient fall risk that can be performed by the fall risk management system of FIG. 1.

Referring now to FIG. 3, an example method 200 of automatically assessing patient fall risk is described. The example method 200 can be performed, for example, using the fall risk management system 102 of FIGS. 1 and 2 described above. The method 200 provides for automatic stratification of patient fall risk based on data automatically gathered and analyzed to compare the data to rules of a healthcare facility in order to determine a patient's level of fall risk. When a nurse assessment to determine a fall score has not yet been performed, other patient information can be used to deduce a patient's fall risk. As additional information is added to the patient's EMR and readings are taken from patient support devices, the patient's fall risk stratification can be automatically updated. This stratification is used to determine whether caregivers need to perform any tasks to prevent falls or whether any alerts to be communicated to caregivers.

At operation 202, data is received from healthcare information systems 104 and patient monitoring devices 106. Data relevant to fall risk is aggregated from multiple sources such as a patient's EMR, a hospital's ADT system, a heart rate monitor attached to the patient, and a mattress sensor pad on the patient's bed.

At operation 204, a fall risk stratification is determined for the patient. This determination is made based on available information for the patient such as their demographic information, current medications, and medical history. In some embodiments, the fall risk stratification is based on a fall score determined by nurse assessments such as the Johns Hopkins Fall Risk Assessment Tool (JHFRAT). Additionally, the stratification of fall risk is based on rules determined by the healthcare facility. Each facility may determine different fall scores or other criteria to distinguish patients of high, medium, and low risk for falls.

At operation 206, tasks and alerts are automatically generated based on the patient's fall risk stratification. Tasks can include preventative measures that caregivers are assigned to complete. Examples of preventative measures include more frequent rounding (checking on the patient more often), putting non-slip socks on the patient, and putting up the guardrails on a patient's bed. The tasks can also be preventative measures that are commanded to patient support devices such as arming a bed-exit alarm on a smart bed. Alerts can include alerts that are communicated to caregivers when a patient's risk stratification increases or when evidence shows that a patient fall is likely to be imminent. The alerts can be communicated through a caregiver mobile application 108*b* or a dashboard 108*a*. Additionally, audible alerts can be sounded in the patient room to inform patients of instructions. In some embodiments, audible alarms are sounded through a nurse call system as well.

Figure 4:
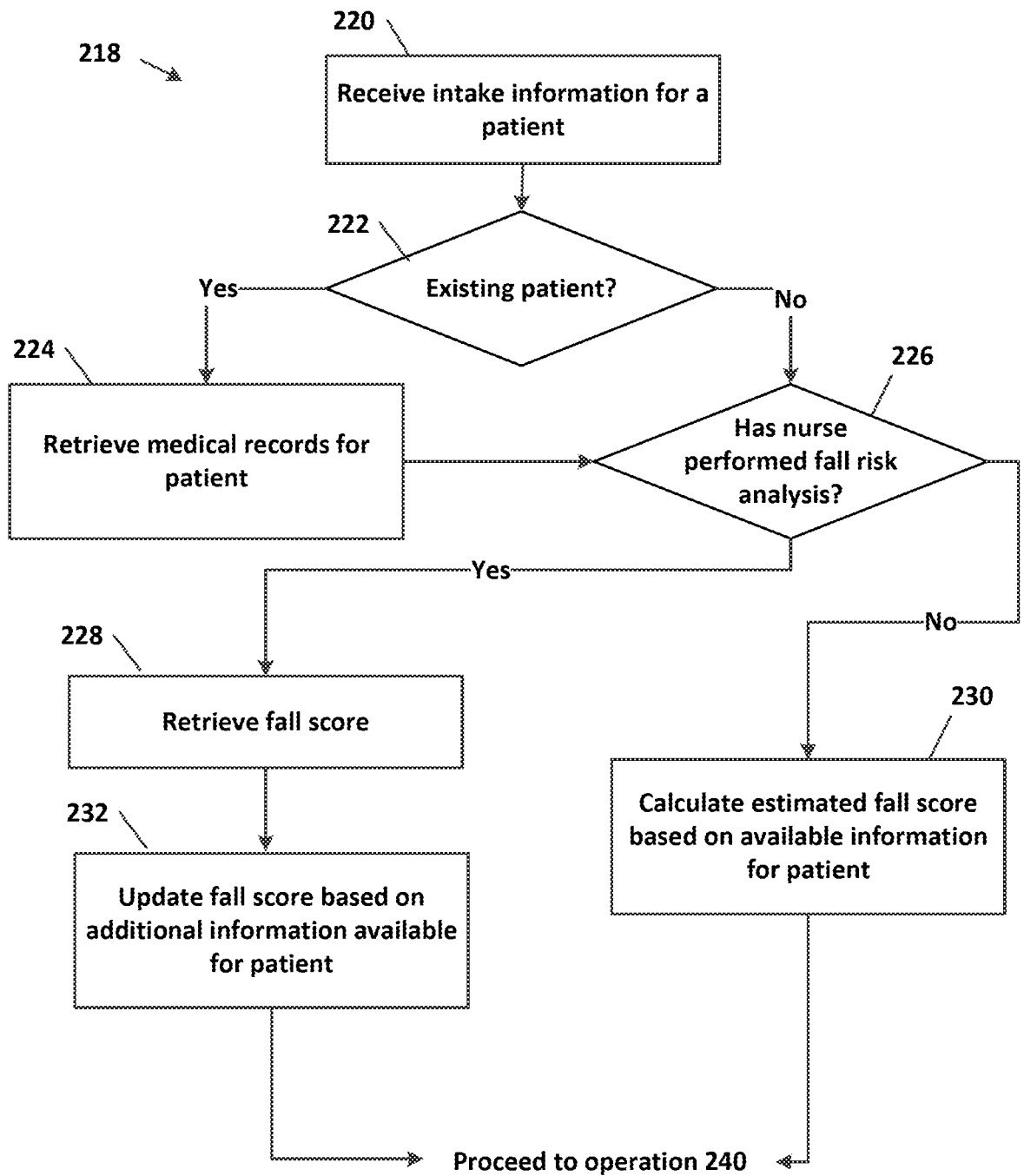
FIG. 4 is a flow chart illustrating a detailed example method of aggregating falls-related data from multiple information sources.

FIG. 4 illustrates a more detailed flow diagram of a method 218 of aggregating falls-related data from multiple sources. Data can be collected from a variety of sources including, for example, an EMR system, an ADT system, or inputs from a caregiver performing an assessment of the patient. In some embodiments, the method 202 is performed by the fall risk management system 102 described in FIGS. 1-2.

At operation 220, intake information for a patient is received. Typically, the intake information will include at least the patient's age, gender, and reason for being in a healthcare facility. Intake information can be gathered from an ADT system through an enterprise gateway 122.

At operation 222, the intake information can be used to determine if the patient was an existing patient of the healthcare facility. For existing patients, the method proceeds to operation 224, where medical records for the patient are retrieved. In some instances, even when the patient is new to the healthcare facility, his or her medical records may be accessible to obtain medical information about the patient. If the patient is new, or if the patient is existing and his or her medical records have been retrieved, the method then proceeds to operation 226.

At operation 226, it is determined whether a caregiver has performed a fall risk analysis of the patient. In some embodiments, the caregiver is a nurse that is performing one of the following tests: Morse Fall Scale, JHFRAT, STRATIFY Risk Assessment Tool, and Schmid Fall Risk Assessment Tool. If a fall risk analysis has been performed, the method proceeds to operation 228 where the fall score determined by the caregiver is retrieved from an information source such as the patient's EMR. The fall score can then be updated at operation 232 if there is any additional information available for the patient that may affect his or her risk for falling.

If a fall risk analysis has not been performed on the patient, the method proceeds to operation 230 where an estimated fall score is calculated based on available medical information for the patient. In some embodiments, a score is not calculated but a general level of fall risk is determined based on the available information for the patient. For example, the patient's age might be indicative of a particular fall risk level.

Figure 5:
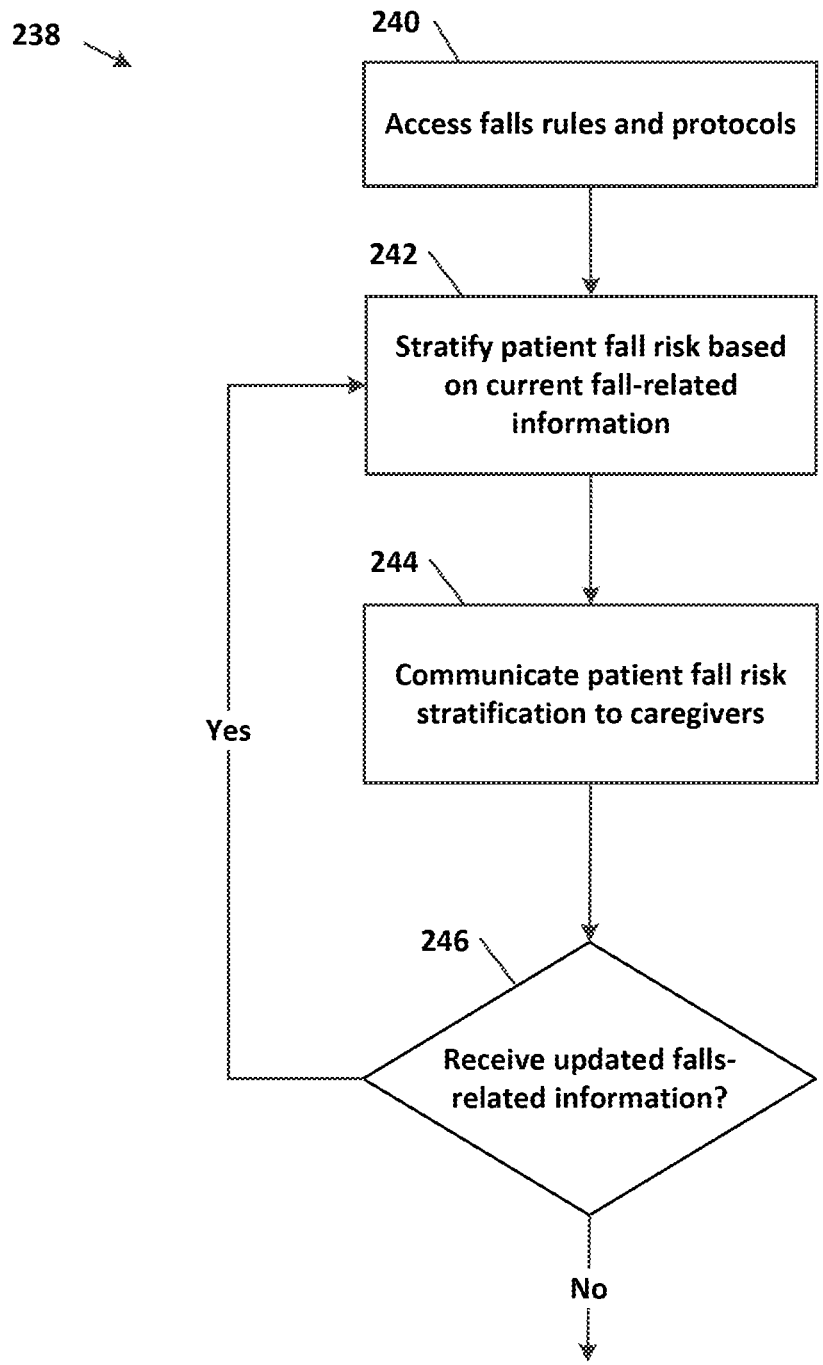
FIG. 5 is a flow chart illustrating a detailed example method of stratifying patient fall risk.

After operation 232 or 230, the method proceeds to operation 240, which is described in FIG. 5. FIG. 5 is a flow diagram of a more detailed method 238 of stratifying patient fall risk. In some embodiments, this method 238 is performed by the risk stratification engine 132 of FIG. 2 in conjunction with the rules manager 130. A level of risk is assigned to each patient based on factors that affect the likelihood of a fall happening to the patient. In some embodiments, the fall risk stratification divides patients into at least three categories: low, medium, and high. In other embodiments, there can be four or more stratification groups for categorizing patient fall risk.

At operation 240, fall-related rules and protocols are accessed. In some embodiments, a rules manager 130 accesses rules for a given healthcare facility from a rules data store 128. Each healthcare facility may have different rules and procedures relating to the prevention and response to patient falls. For example, one set of rules may define the fall risk scores of patients that fall into high, medium, and low risk for falls. These could be based on fall assessment scores. Other rules could govern the tasks that caregivers should perform to prevent falls based on a patient's risk stratification or how caregivers should respond to an alert relating to a heightened fall risk.

At operation 242, the patient is stratified based on falls-related information that is currently available for the patient. This stratification assigns the patient to a fall risk category such as high, medium, or low. This stratification process can be based on a fall risk score calculated for the patient, as well as other factors such as medical history, what medications the patient is currently taking, and patient age. In some embodiments, this stratification process is performed by a risk stratification engine 132 that accesses information from a clinical data repository 120, one or more healthcare information systems 104, and optionally one or more patient support devices 106. Rules pertinent to the healthcare facility and patient are determined by the rules manager 130 and are communicated to the risk stratification engine 132 in order to assess which category of fall risk should be assigned to a patient.

At operation 244, the patient fall risk stratification is communicated to caregivers. This communication can occur through a caregiver communication system 108, such as the dashboard 108a, a caregiver mobile application 108b, or caregiver call systems 108c. In some embodiments, the patient fall risk stratification can also be communicated to a healthcare information system 104 such as an EMR system 104a. In some embodiments, this communication is mediated through an enterprise gateway 122.

At operation 246, the fall risk management system 102 checks for new, updated falls-related information pertinent to the healthcare facility and/or patient. If there is new information available, the method proceeds to operation 242, where the patient's fall risk is stratified again based on the updated information. If there is no updated information, the method proceeds to operation 260, which is described in FIG. 6.

Figure 6:
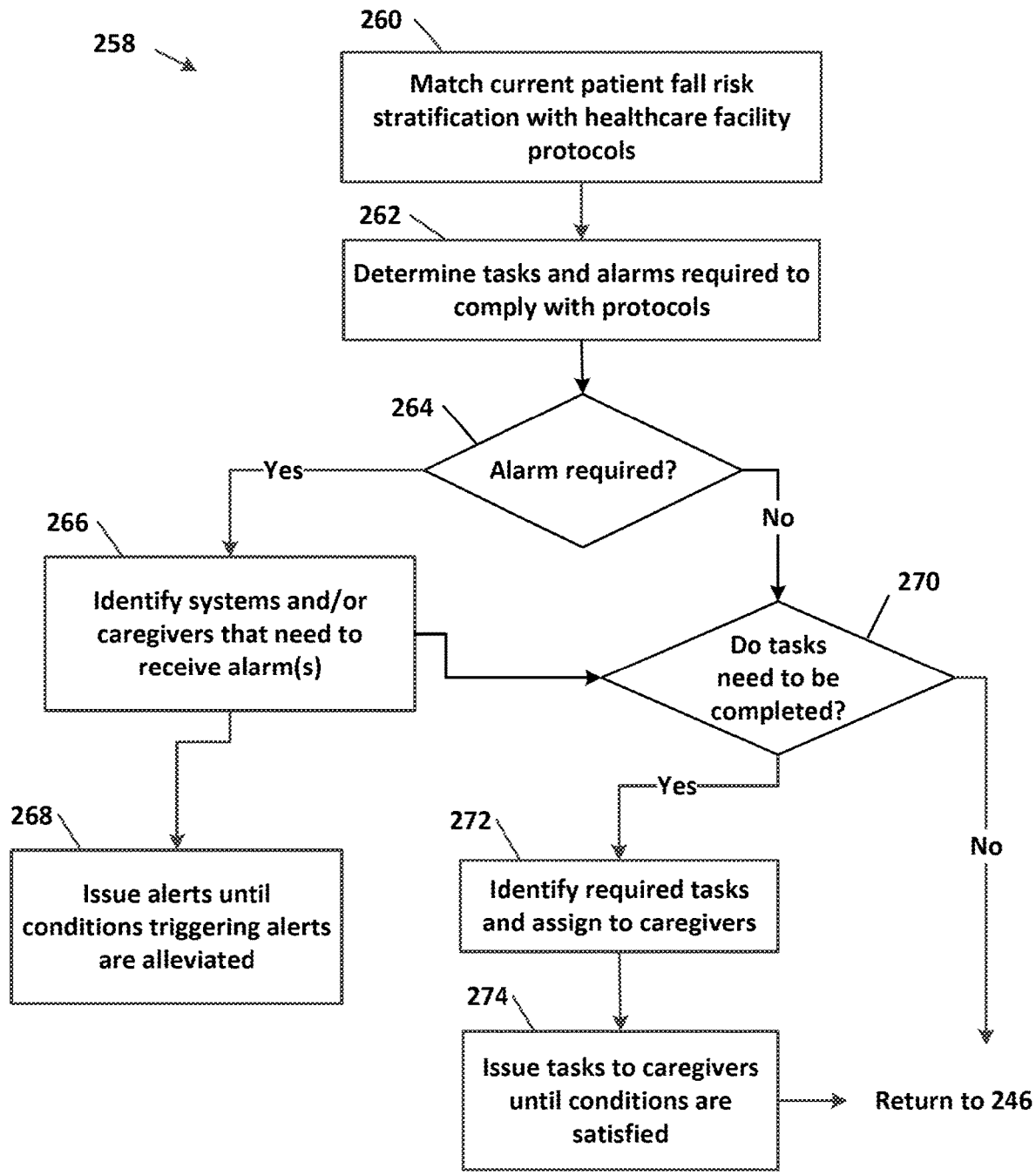
FIG. 6 is a flow chart illustrating a detailed example method of generating tasks and alerts based on a patient's fall risk stratification.
Figure 7:
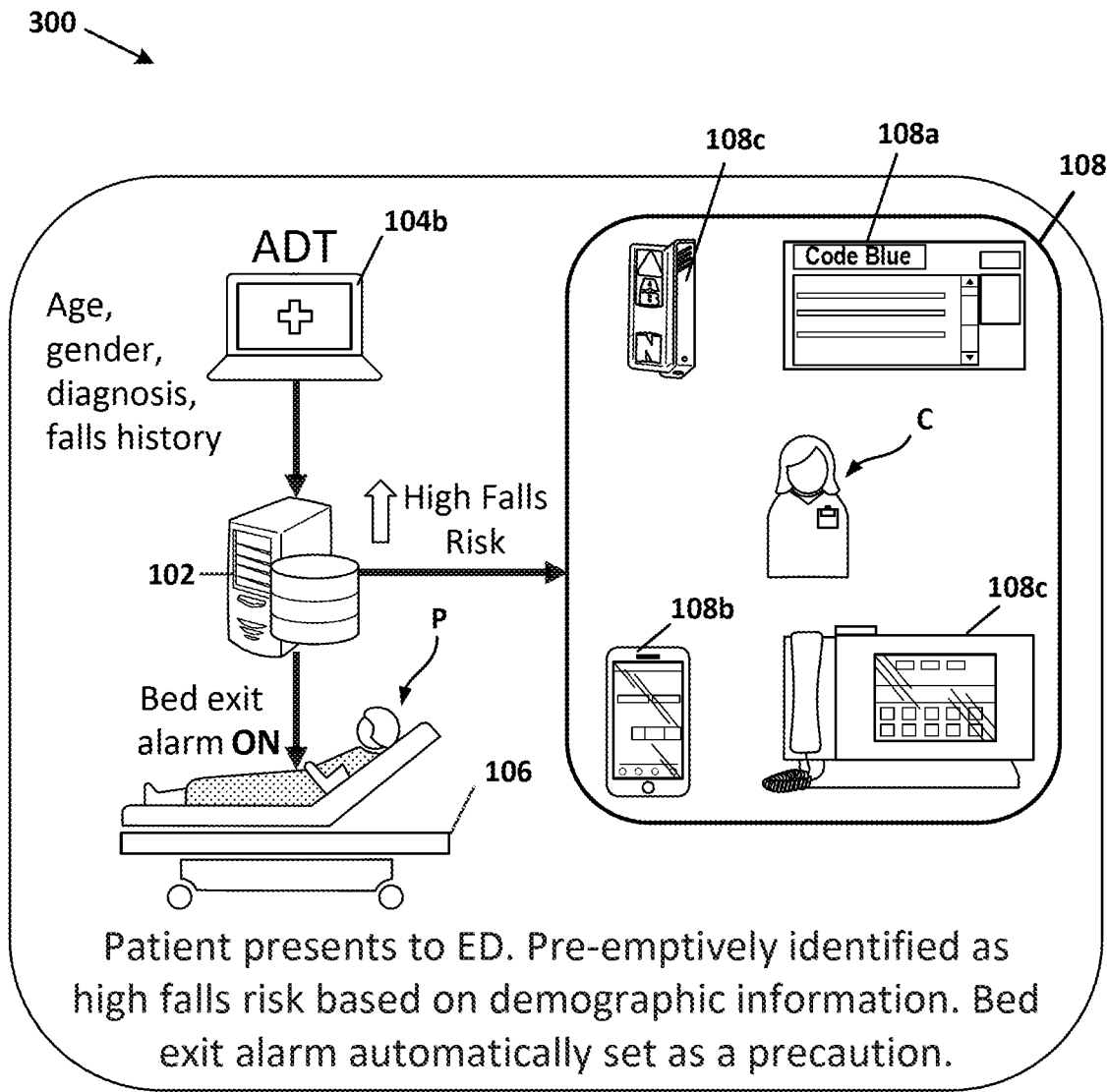
FIG. 7 is a diagram illustrating an example of how the fall risk management system could operate in a hospital setting.

FIG. 6 is a flow diagram of a more detailed method 258 of generating tasks and alerts based on a patient's fall risk stratification. Tasks and alerts can be automatically communicated to caregivers via caregiver communication systems such as a caregiver mobile application 108b. The tasks and alerts applicable to a patient can be determined based on a healthcare facility's falls-related rules and procedures.

At operation 260, the patient's current fall risk stratification is matched to healthcare facility rules and protocols applicable to that risk stratification. In some embodiments, this step is performed by a rules manager 130. The rules manager 130 accesses a rules data store 128 and determines the current risk stratification for a patient by communicating with a risk stratification engine 132. In other embodiments, the patient's risk stratification can be accessed from the patient's EMR.

At operation 262, tasks and alerts required to comply with the healthcare facility protocols are determined. In some embodiments, the tasks are determined by a task manager 134 and alerts are determined by an alert manager 138. Examples of tasks include checking on high risk patients more frequently. An example of an alert is to notify a caregiver if a patient's fall risk score suddenly increases.

At operation 264, if an alert is required for the current patient risk stratification (usually due to a change in stratification), the method proceeds to operation 266. If an alert is not required, the method proceeds to operation 270.

At operation 266, systems and/or caregivers that need to receive one or more alerts are identified. In some embodiments, this is performed by the alert manager 138. The caregivers may be selected based on their role, work schedule, and assignments. For example, alerts might be communicated to a nurse and a doctor assigned to a particular patient. Additionally, a facility's procedures might call for communicating an alert to a dashboard 108a displaying information for that patient. At operation 368, the alerts continue until the patient risk stratification changes or the conditions triggering the alert are alleviated. At the same time, the method proceeds to operation 270.

At operation 270, if tasks need to be completed to comply with protocols for a given patient risk stratification, the method proceeds to operation 272. If no tasks are required at the current time based on the current risk stratification of the patient, the method returns to operation 246 in FIG. 5. If tasks need to be completed to comply with facility rules, the required tasks for the situation are identified and assigned to appropriate caregivers on duty in operation 272. In some embodiments, a task manager 134 operates to identify tasks and the appropriate caregivers to complete those tasks.

At operation 274, the identified tasks are communicated to caregivers that are scheduled and assigned to care for a given patient. The tasks will continue to be communicated to those caregivers until the tasks are completed. Once the task manager 134 receives an indication that all required tasks are completed, the method can return to operation 246 in FIG. 5.

FIGS. 7-10 illustrate an example of how a fall risk management system 102 might operate within a hospital. In view 300 shown in FIG. 7, a diagram shows a patient P has arrived at the emergency department of the hospital. The hospital's ADT system 104a records intake information about the patient P as he or she is admitted. The ADT 104a records information regarding the patient's age, gender, diagnosis, and falls history. This information is communicated to the fall risk management system 102 where it is processed to stratify the patient's risk for falling. Note that in this scenario, a nurse assessment of fall risk (such as Morse score) has not yet been performed.

The fall risk management system 102 calculates the patient's fall risk to be high based on the patient's demographic information and falls history. A command is communicated to the patient's smart bed 106c to set the bed exit alarm automatically. Additionally, the patient's high falls risk stratification is communicated to a caregiver mobile application so that a caregiver C is advised of the patient high fall risk. In some instances, there might be an alert communicated to the caregiver C to ensure that he or she notices that a new patient with a high falls risk is under his or her care.

Figure 8:
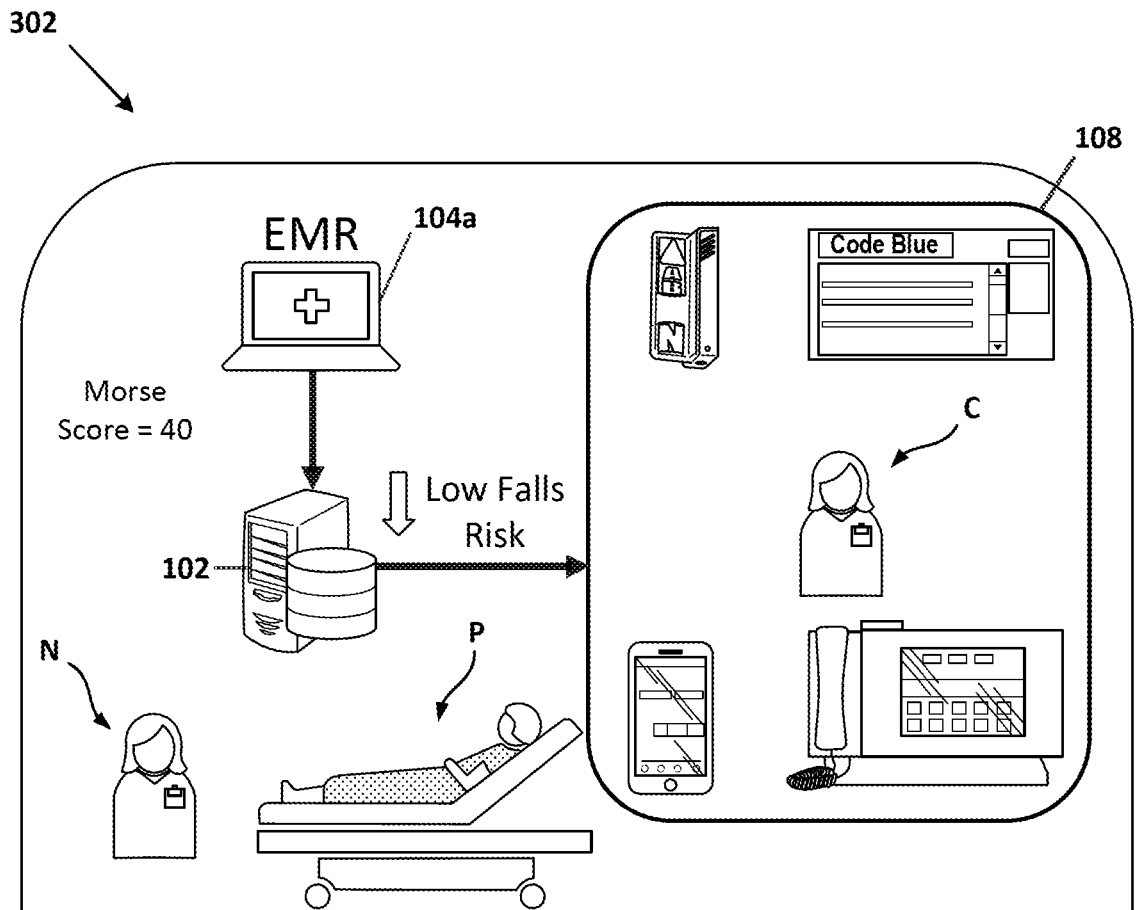
FIG. 8 is another diagram further illustrating the example of FIG. 7.

FIG. 8 illustrates another view 302 of the diagram, where a nurse N has performed a risk assessment of the patient and has recorded a fall risk score (Morse score) in the patient's EMR 104a. In this example, the patient P has a Morse score of 40. The fall risk management system 102 ingests the updated data from the EMR 104a and determines, based at least in part on the patient's Morse score, that the patient's fall risk level is low. The hospital's risk stratification rules call for a lower fall risk stratification when a patient has a Morse score of 40. The updated falls risk stratification for the patient P is communicated to one or more of a dashboard 108a, a caregiver mobile application 108b, and nurse call systems 108c. Additionally, the protocols and tasks required for the patient are updated and communicated to caregivers through the caregiver application 108b or other means.

Figure 9:
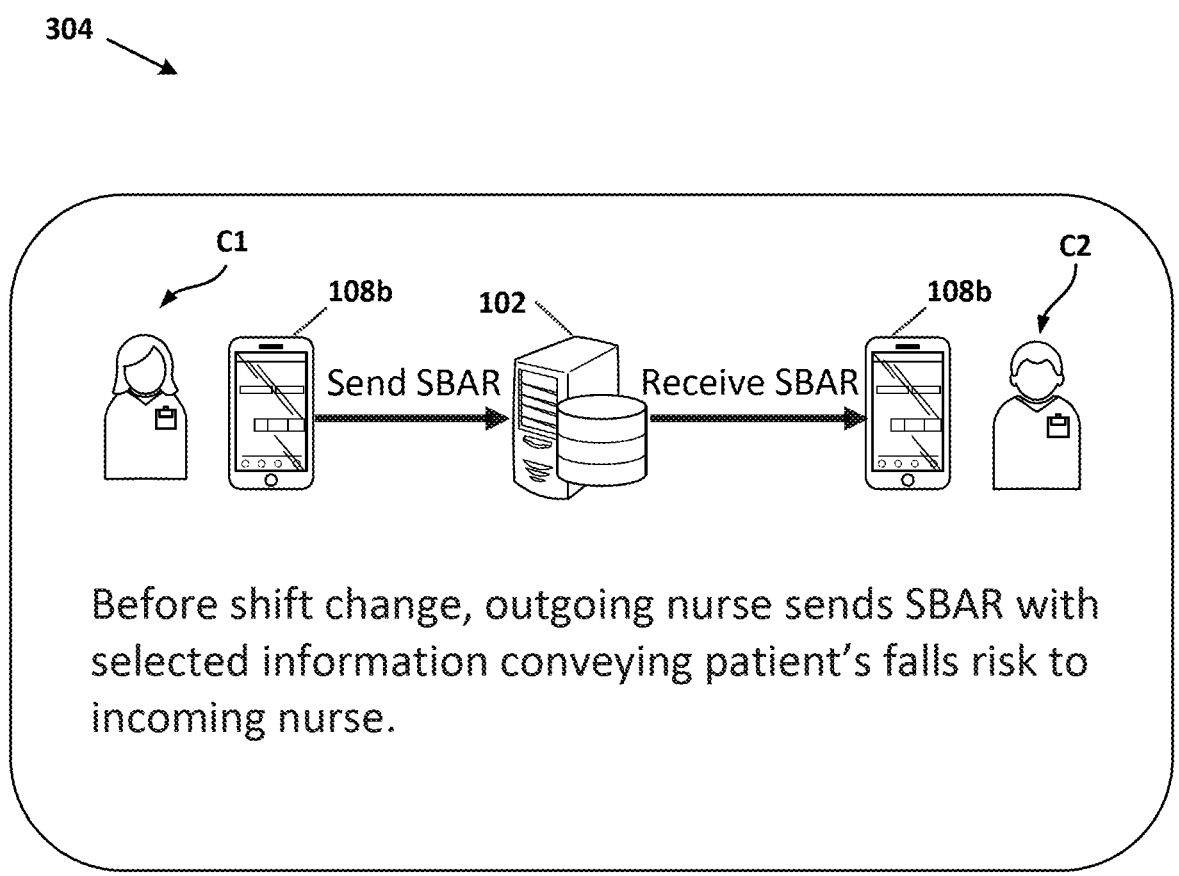
FIG. 9 is another diagram further illustrating the example of FIG. 7.

FIG. 9 illustrates another view 304 of the diagram, when an SBAR handoff is occurring. A first caregiver C1 prepares an SBAR report for a patient on her mobile device and sends it to the fall risk management system 102 at the end of her shift. A second caregiver C2 that is starting his shift receives the SBAR report from the fall risk management system 102 on his mobile device. This communication ensures that the caregivers are always updated on necessary information to properly care for a patient and prevent falls.

Figure 10:
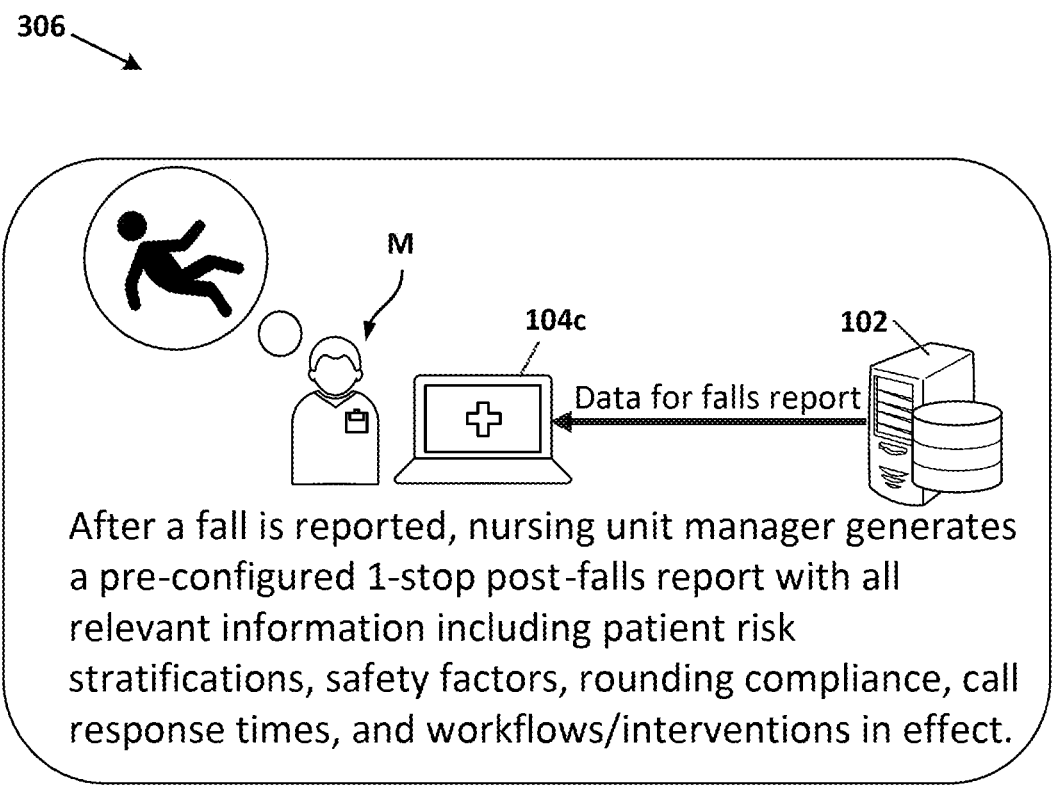
FIG. 10 is another diagram further illustrating the example of FIG. 7.

FIG. 10 illustrates another view 306 of the diagram. Here a nursing unit manager M is using an administrator computing device 104c to request a post-fall report including various information relating to fall risk mitigation. The data is received from the fall risk management system 102 and used to generate the report. In this example, the report includes information about patient risk stratifications, safety factors, rounding compliance, call response times, and workflows and interventions that were in effect.

Figure 11:
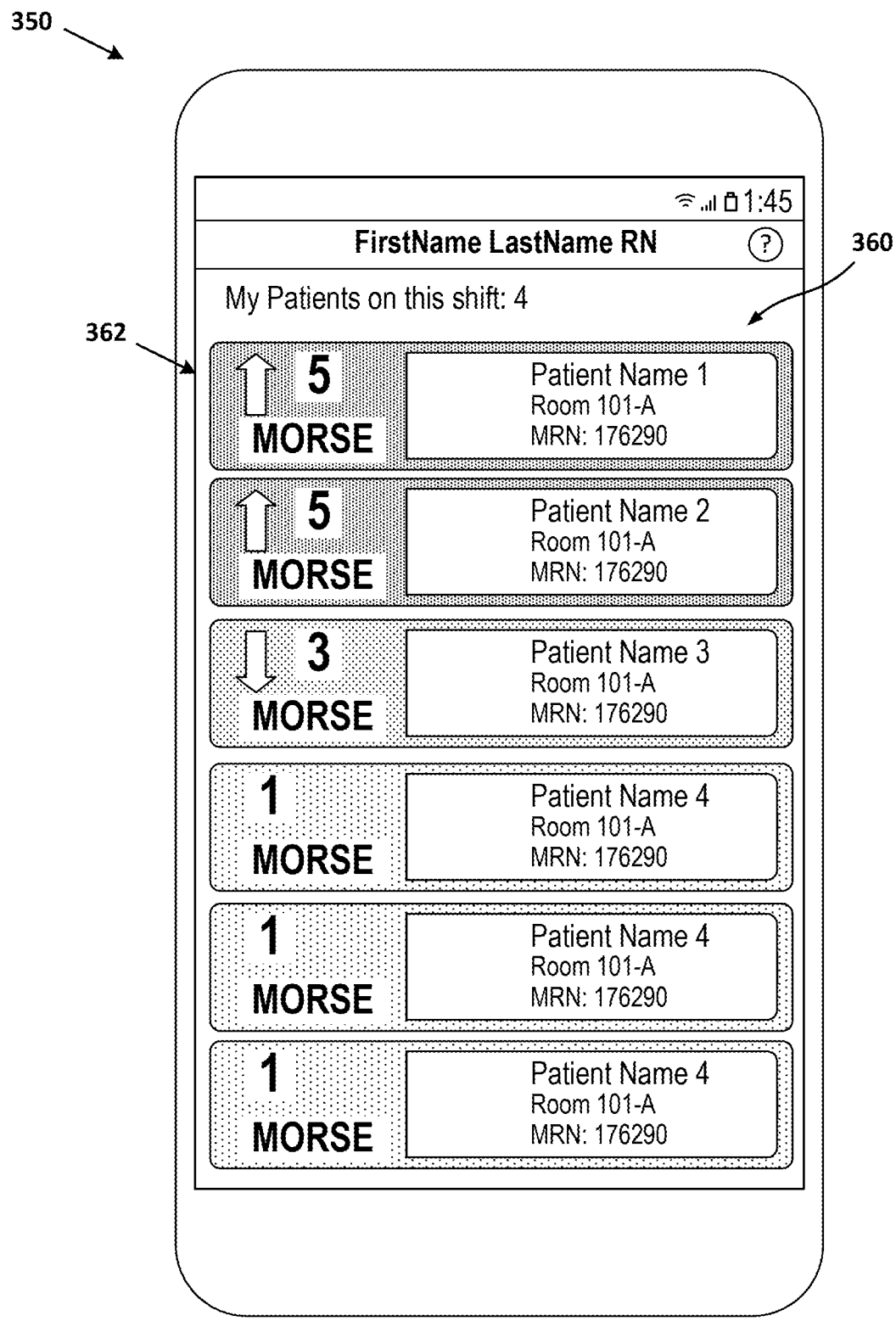
FIG. 11 shows an example graphical user interface displayed on a caregiver mobile application.

FIG. 11 shows an example view 350 of a graphical user interface (GUI) 360 displayed on a caregiver mobile device 362. In this view, patients that a nurse is responsible for during her shift are displayed. Color coding and numerical indicators show the patients' fall risk.

Figure 12:
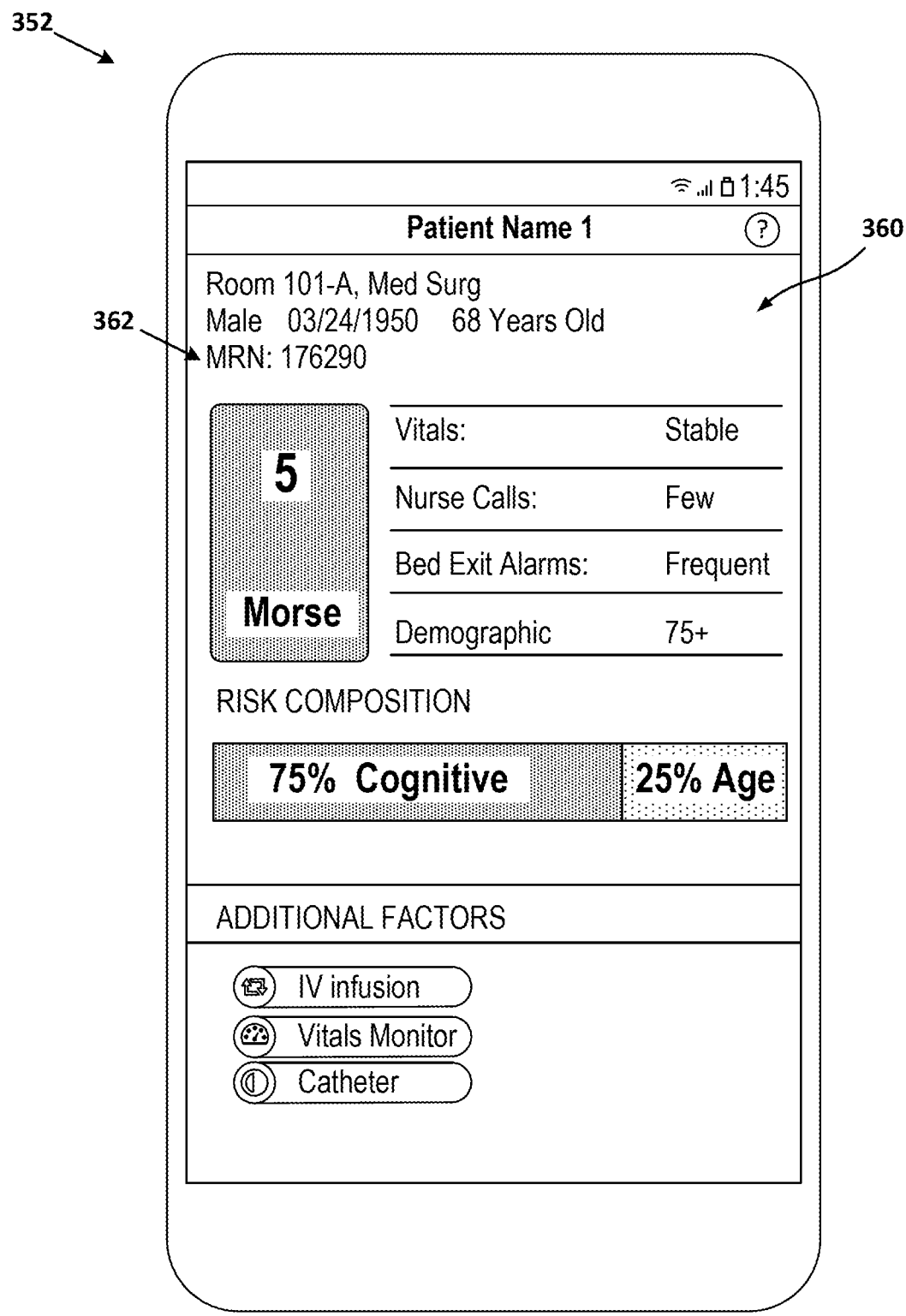
FIG. 12 shows another view of the example graphical user interface of FIG. 11.

FIG. 12 shows another view 352 of the GUI 360. In this view, the patient #1 has been selected and details about the patient are displayed on the caregiver mobile device 362. Some of the information that is displayed includes the patient's gender, age, room location, Morse score, vitals status, number of nurse calls, frequency of bed exit alarms, and age demographic. In the example of FIG. 12, a risk composition is also displayed, indicating that 75% of the risk is for cognitive reasons and 25% is attributable to the patient's age. Additional factors are listed at the bottom of the screen and include "IV infusion," "Vitals monitor," and "Catheter."

Figure 13:
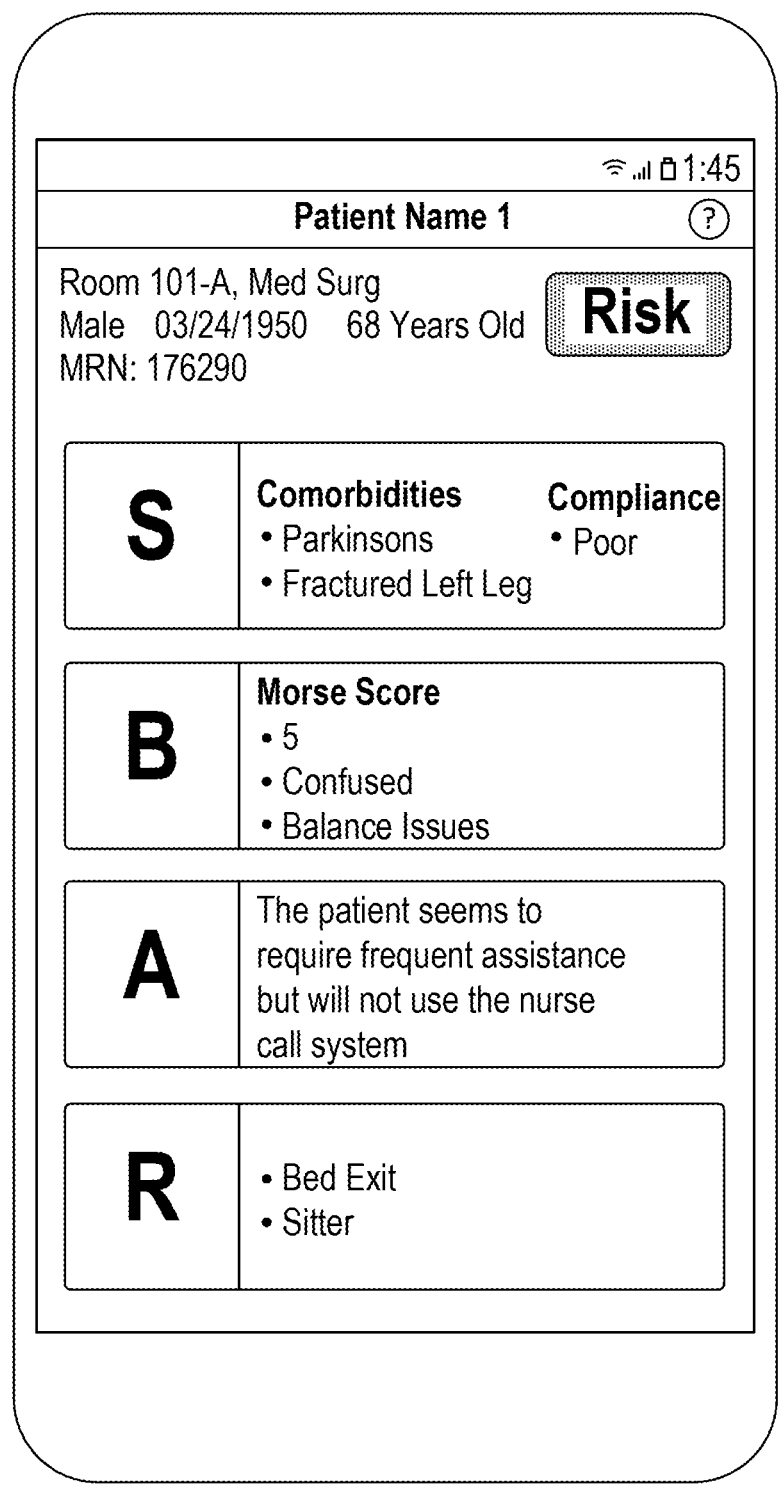
FIG. 13 shows another view of the example graphical user interface of FIG. 11.

FIG. 13 shows another view 354 of the GUI 360 displaying an SBAR report on the caregiver mobile device 362. This SBAR report will be sent to the caregiver taking over care of patient #1 at the shift change.

Figure 14:
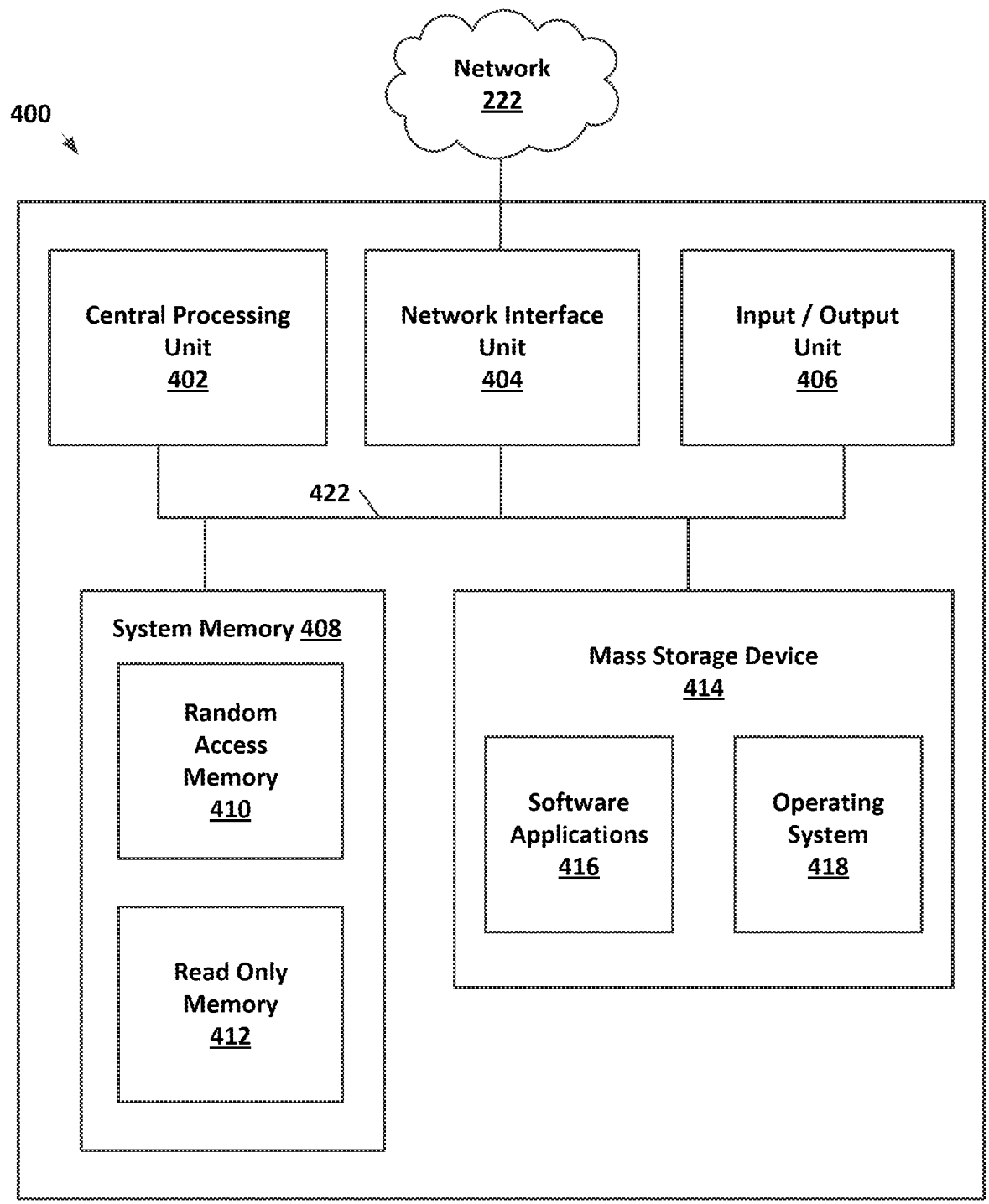
FIG. 14 is a schematic block diagram of an example computing device usable to implement aspects of the fall risk management system of FIG. 1.

FIG. 14 is a block diagram illustrating an example of the physical components of a computing device 400. The computing device 400 could be any computing device utilized in conjunction with the fall risk management system 102 such as a caregiver communication device 108 or the computing device 142 of FIG. 2.

In the example shown in FIG. 14, the computing device 400 includes at least one central processing unit ("CPU") 402, a system memory 408, and a system bus 422 that couples the system memory 408 to the CPU 402. The system memory 408 includes a random access memory ("RAM") 410 and a read-only memory ("ROM") 412. A basic input/output system that contains the basic routines that help to transfer information between elements within the computing device 400, such as during startup, is stored in the ROM 412. The computing system 400 further includes a mass storage device 414. The mass storage device 414 is able to store software instructions and data such as falls-related data extracted from electronic healthcare records.

The mass storage device 414 is connected to the CPU 402 through a mass storage controller (not shown) connected to the system bus 422. The mass storage device 414 and its associated computer-readable storage media provide non-volatile, non-transitory data storage for the computing device 400. Although the description of computer-readable storage media contained herein refers to a mass storage device, such as a hard disk or solid state disk, it should be appreciated by those skilled in the art that computer-readable data storage media can include any available tangible, physical device or article of manufacture from which the CPU 402 can read data and/or instructions. In certain embodiments, the computer-readable storage media comprises entirely non-transitory media.

Computer-readable storage media include volatile and non-volatile, removable and non-removable media implemented in any method or technology for storage of information such as computer-readable software instructions, data structures, program modules or other data. Example types of computer-readable data storage media include, but are not limited to, RAM, ROM, EPROM, EEPROM, flash memory or other solid state memory technology, CD-ROMs, digital versatile discs ("DVDs"), other optical storage media, magnetic cassettes, magnetic tape, magnetic disk storage or other magnetic storage devices, or any other medium which can be used to store the desired information and which can be accessed by the computing device 400.

According to various embodiments, the computing device 400 can operate in a networked environment using logical connections to remote network devices through a network 421, such as a wireless network, the Internet, or another type of network. The computing device 400 may connect to the network 421 through a network interface unit 404 connected to the system bus 422. It should be appreciated that the network interface unit 404 may also be utilized to connect to other types of networks and remote computing systems. The computing device 400 also includes an input/output controller 406 for receiving and processing input from a number of other devices, including a touch user interface display screen, or another type of input device. Similarly, the input/output controller 406 may provide output to a touch user interface display screen or other type of output device.

As mentioned briefly above, the mass storage device 414 and the RAM 410 of the computing device 400 can store software instructions and data. The software instructions include an operating system 418 suitable for controlling the operation of the computing device 400. The mass storage device 414 and/or the RAM 410 also store software instructions, that when executed by the CPU 402, cause the computing device 400 to provide the functionality discussed in this document. For example, the mass storage device 414 and/or the RAM 410 can store software instructions that, when executed by the CPU 402, cause the computing system 400 to stratify patients' fall risk.

Although various embodiments are described herein, those of ordinary skill in the art will understand that many modifications may be made thereto within the scope of the present disclosure. Accordingly, it is not intended that the scope of the disclosure in any way be limited by the examples provided.

What is claimed is:

1. A system for automatically assessing patient fall risk, the system comprising:
   at least one processor; and
   memory encoding instructions which, when executed by the at least one processor, cause the at least one processor to:
   a) automatically aggregate falls-related data for a patient from one or more healthcare information systems;
   b) access falls-related rules for a healthcare facility administering care to the patient, the falls-related rules defining criteria for fall risk stratifications and protocols for each fall risk stratification, and the falls-related rules being custom for the healthcare facility;
   c) stratify fall risk of the patient based on healthcare facility falls-related rules and falls-related data associated with the patient;
   d) automatically generate tasks and alerts based on a fall risk stratification of the patient and the healthcare facility falls-related rules, wherein the tasks and alerts are communicated through a mobile application to caregivers assigned to the patient; and
   e) repeat steps a-d until the healthcare facility is no longer administering care to the patient,
      wherein the system is configured to generate commands to one or more external devices to automatically perform tasks or adjustments to reduce the patient's fall risk based on the patient's risk stratification, including to enable a bed rail associated with a bed that is supporting the patient, and
      wherein at least one of the tasks is communicating a command to a bed exit alarm to automatically arm the bed exit alarm when the fall risk stratification is high.

2. The system of claim 1, wherein the falls-related data is further aggregated from one or more patient monitoring devices associated with the patient.

3. The system of claim 2, wherein the one or more patient monitoring devices include one or more of a mattress pad sensor, a vital signs monitor, a smart bed, and a spot monitor.

4. The system of claim 1, wherein the falls-related data includes one or more of patient age, patient gender, patient height, patient weight, medications the patient is currently taking, and current medical condition of the patient.

5. The system of claim 1, wherein the healthcare information systems include one or more of electronic medical record (EMR) systems, admit/discharge/transfer (ADT) systems, and healthcare administration computing systems.

6. The system of claim 1, wherein the falls-related data for the patient includes a fall score determined from a caregiver assessment.

7. The system of claim 1, wherein the falls-related data for the patient excludes a fall score determined from a caregiver assessment.

8. The system of claim 1, wherein the alerts are communicated through a patient dashboard.

9. The system of claim 1, wherein the fall risk stratification for the patient is communicated in a "Situation, Background, Assessment, Recommendation" (SBAR) report from one caregiver to another.

10. One or more computer-readable media having computer-executable instructions embodied thereon that, when executed by one or more computing devices, cause the computing devices to:
receive intake information for a patient at a healthcare facility;
access any available medical information for the patient;
access fall-related rules for the healthcare facility, the falls-related rules defining fall risk stratifications and protocols for preventing falls, and the falls-related rules being custom for the healthcare facility;
before receiving a fall risk score input from a caregiver analysis, determine a fall risk stratification for the patient based on the intake information, available medical information for the patient, and falls-related rules for the healthcare facility;
communicate the fall risk stratification to one or more caregiver communication systems; and
generate and communicate one or more tasks to one or more caregivers assigned to the patient through the one or more caregiver communication systems, the tasks being generated based on the falls-related rules, wherein the tasks and alerts are communicated through a mobile application to caregivers assigned to the patient;
repeat execution of the computer-executable instructions until the healthcare facility is no longer administering care to the patient,
wherein the computing devices are configured to generate commands to one or more external devices to automatically perform tasks or adjustments to reduce the patient's fall risk based on the patient's risk stratification, including to enable a bed rail associated with a bed that is supporting the patient, and
wherein at least one of the tasks is communicating a command to a bed exit alarm to automatically arm the bed exit alarm when the fall risk stratification is high.

11. The one or more computer-readable media of claim 10, wherein the computer-executable instructions further cause the computing devices to:
receive the fall risk score input from the caregiver analysis;
update the fall risk stratification for the patient based on the intake information, available medical information for the patient, fall risk score, and falls-related rules for the healthcare facility;
communicate the updated patient fall risk stratification to the one or more caregiver communication systems; and
generate and communicate one or more updated tasks or alerts to the one or more caregivers assigned to the patient through the one or more caregiver communication systems.

12. The one or more computer-readable media of claim 10, wherein the computer-executable instructions further cause the computing devices to:
receive updated medical information for the patient;
update the fall risk stratification for the patient based on the updated medical information and falls-related rules for the healthcare facility;
communicate the updated patient fall risk stratification to the one or more caregiver communication systems; and
generate and communicate one or more updated tasks or alerts to the one or more caregivers assigned to the patient through the one or more caregiver communication systems.

13. The one or more computer-readable media of claim 10, wherein the updated medical information is received from an electronic health record system.

14. The one or more computer-readable media of claim 10, wherein the updated medical information is received from a patient support device.

15. A computer-implemented method of managing patient fall risk in a healthcare facility, the method comprising:
a) automatically aggregating, at a fall risk management system, falls-related data for a patient from one or more healthcare information systems;
b) accessing, from a rules data store, falls-related rules for a healthcare facility administering care to the patient, the falls-related rules defining criteria for fall risk stratifications and protocols for each fall risk stratification, and the falls-related rules being custom for the healthcare facility;
c) stratifying fall risk of the patient based on healthcare facility falls-related rules and falls-related data associated with the patient;
d) automatically generating and communicating tasks and alerts to one or more devices, the tasks and alerts being based on a fall risk stratification of the patient and the healthcare facility falls-related rules, wherein the tasks and alerts are communicated through a mobile application to caregivers assigned to the patient; and
e) repeating steps a-d until the healthcare facility is no longer administering care to the patient,
wherein the fall risk management system is configured to generate commands to one or more external devices to automatically perform tasks or adjustments to reduce the patient's fall risk based on the patient's risk stratification, including to enable a bed rail associated with a bed that is supporting the patient, and
wherein at least one of the tasks is communicating a command to a bed exit alarm to automatically arm the bed exit alarm when the fall risk stratification is high.

16. The method of claim 15, wherein the falls-related data is further aggregated from one or more of a mattress pad sensor, a vital signs monitor, a smart bed, and a spot monitor.

17. The method of claim 15, wherein the falls-related data includes a fall score determined from a caregiver assessment.

\* \* \* \* \*